United States Patent [19]
Berzofsky

[11] Patent Number: 5,939,074
[45] Date of Patent: Aug. 17, 1999

[54] MULTIDETERMINANT PEPTIDE ANTIGENS

[75] Inventor: Jay A. Berzofsky, Bethesda, Md.

[73] Assignee: The United States of America as represented by the Department of Health and Human Services, Washington, D.C.

[21] Appl. No.: 08/407,252

[22] Filed: Mar. 20, 1995

Related U.S. Application Data

[63] Continuation of application No. 08/109,730, Aug. 19, 1993, which is a continuation of application No. 07/751,998, Aug. 29, 1991, which is a continuation-in-part of application No. 07/492,318, Feb. 28, 1990, Pat. No. 5,081,226, which is a continuation of application No. 07/014,430, Feb. 12, 1987, which is a continuation-in-part of application No. 06/947,935, Dec. 30, 1986, said application No. 07/751,998, is a continuation-in-part of application No. 07/148,692, Jan. 26, 1988, and a continuation of application No. 07/222,684, Jul. 21, 1988, Pat. No. 5,030,499.

[51] Int. Cl.⁶ .......................... A61K 39/21; A61K 39/38; A61K 39/385; A61K 39/12
[52] U.S. Cl. .................... 424/208.1; 424/184.1; 424/188.1; 424/193.1; 424/204.1; 530/324; 435/326
[58] Field of Search .......................... 530/324; 435/326; 424/208.1, 186.1, 188.1, 193.1, 204.1

[56] References Cited

U.S. PATENT DOCUMENTS 4,943,628 7/1990 Rosen et al. ........................... 530/326

FOREIGN PATENT DOCUMENTS

| | | |
|---|---|---|
| 0273716 | 7/1988 | European Pat. Off. . |
| A-0 273 716 | 7/1988 | European Pat. Off. . |
| A-0 279 688 | 8/1988 | European Pat. Off. . |
| A-0 317 804 | 5/1989 | European Pat. Off. . |
| 0328403 | 8/1989 | European Pat. Off. . |
| A-0 328 403 | 8/1989 | European Pat. Off. . |
| WO-A-89 02277 | 3/1989 | WIPO . |
| WO-A-90 00901 | 2/1990 | WIPO . |
| A-0 370 458 | 5/1990 | WIPO . |
| WO-A-91 04045 | 4/1991 | WIPO . |
| WO-A-92 05800 | 4/1992 | WIPO . |

OTHER PUBLICATIONS

Muesing et al., Nature, vol. 313, Feb. 7, 1985, pp. 450–458.
Clerici et al, Nature, vol. 339, pp. 383–385 (1989).
Berzofsky et al, Nature, vol. 334, pp. 706–708 (1988).
Hale et al., International Immunology, vol. 1, No. 4, pp. 409–415 (1989).
Chakrabarti, et al., 1986, "Expression of the HTLV–III. . . ." Nature 320:535–537.
Robey, et al., 1986 "Prospect for prevention of human. . . ." PNAS 83:7023–7027.
Cease, et al., 1987, "Helper T cell antigenic site identification. . . ." PNAS 84:4249–4253.
Sternberg, et al., 1987, "Prediction of antigenic determinants. . . ." FEBS Letters 218:231–237.
Milich, et al., 1986, "Nonoverlapping T and B cell. . . ." J. Exp. Med. 164:532–547.
Zarling, et al., 1986, "T–cell responses to human AIDS virus. . . ." Nature 323:344–346.
DeLisi, et al., 1985, "T–cell antigenic sites tend. . . ." PNAS 82:7048–7052.
Wain–Hobson, et al., 1985, "Nucleotide sequence of the AIDS. . . ." Cell 40:9–17.
Sternberg, et al., 1987, FEBS Letters 218:231–37.
Cease, et al., 1987, PNAS 84:4249–4253.

*Primary Examiner*—Lynette F. Smith
*Assistant Examiner*—Brett Nelson
*Attorney, Agent, or Firm*—Townsend and Townsend and Crew LLP

[57] ABSTRACT

This invention relates to the selection and preparation of synthetic peptides which stimulate helper T lymphocyte response to HIV in a wide range of human subjects. These multideterminant peptides are, therefore, useful for the production of vaccines against HIV infection and for diagnostic procedures to test for HIV seroconversion.

12 Claims, 4 Drawing Sheets

MULTIDETERMINANT PEPTIDE ANTIGENS

RELATED APPLICATIONS

This application is a continuation of U.S. application Ser. No. 08/109,730, filed on Aug. 19, 1993, which is a continuation of U.S. application Ser. No. 07/751,998, filed on Aug. 29, 1991, which is a continuation in part of U.S. application Ser. No. 07/492,318, filed on Feb. 28, 1990 (now U.S. Pat. No. 5,081,226), which is a continuation of U.S. application Ser. No. 07/014,430, filed on Feb. 12, 1987, which is a continuation in part of U.S. application Ser. No. 06/947,935, filed on Dec. 30, 1986. Priority application Ser. No. 07/751, 998 is also a continuation in part of U.S. application Ser. No. 07/148,692, filed on Jan. 26, 1988, and is also a continuation of U.S. application Ser. No. 07/222,684 filed on Jul. 21, 1988 (now U.S. Pat. No. 5,030,499). All of the above noted priority applications/patents are incorporated herein by reference.

FIELD OF THE INVENTION

The invention is directed to a method for the selection of peptides useful for production of vaccine(s) against HIV infection or as components of a therapeutic mixture or as components of a diagnostic kit for HIV infection. The instant application also describes a series of peptides selected by the method.

BACKGROUND OF THE INVENTION

Whole virus vaccines against HIV, live attenuated or killed offer the potential to stimulate immunity to the broadest array of antigenic determinants of the virus. However, they also may contain structures developed by the virus to evade the immune system, such as suppressive epitopes or masking carbohydrates, or structures which elicit deleterious effects such as enhancing antibodies that increase viral infectivity (Takeda, A. et al. *Science* 242:580–583. (1988); Robinson, W. E. Jr. et al., *Proc. Nati. Acad. Sci. USA* 86:4710–4714 (1989); Robinson, W. E., Jr. et al.; *Proc. Natl. Acad. Sci. USA* 87:3185–3189 (1990); Halstead, S. B. *Science* 239:476–481 (1988)) or antibodies or T cells that may contribute to immunodeficiency in the case of HIV (Weinhold, K. J. et al., *J. Immununol* 142:3091–3097 (1989); Siliciano, R-F.; et al., *Cell* 54:561–575 (1988); Mittler, R. S. and M. K. Hoffmann, *Science* 245:1380–1382 (1989); Golding, H. et al., *J. Clin. Invest.* 83:1430–1435 (1989)). In addition, for a retrovirus such as HIV, concerns about the safety of live attenuated or even killed whole viral vaccines may make them unacceptable to many potential recipients. Purified subunit vaccines have less safety risk, but still may suffer from the other problems of whole virus vaccines. Indeed, because the virus has evolved to evade the immune system, evolution may have favored the development of viral proteins that are hardly optimal as vaccines. Thus, in contrast to enzymes which have been honed by evolution to be the best structures for catalyzing their reactions, viral proteins may leave the scientist with considerable opportunities to improve on nature for the development of better vaccines (Berzofsky, J. A., *J. Clin. Invest.* 82:1811–1817 (1988)).

To rationally design highly engineered synthetic or recombinant antiviral vaccines, one needs considerable knowledge about the workings of the immune system, and in particular, about the immune response to structures expressed by the virus. The present inventors have initiated such an approach by attempting to identify antigenic determinants recognized by cytotoxic T lymphocytes (CTL) (Takahashi, H. et al., *Proc. Natl. Acad. Sci. USA* 85:3105–3109 (1988); Takahashi, H. et al, *Science* 246:118–121 (1989); Takahashi, H. et al., *J. Exp. Med.* 170:2023–2035 (1989); Takahashi, H. et al., *J. Exp. Med.* 171:571–576 (1990); Hosmalin, A. et al, *Proc. Natl. Acad. Sci. USA* 87:2344–2348 (1990)) and by helper T cells that would be required for either a CTL or an antibody response (Cease, K. B. et al., *Proc. Natl. Acad. Sci. USA* 84:4249–4253 (1987); Berzofsky, J. A. et al. *Nature* 334:706–708 (1988); Clerici, M. et al., *Nature* 339:383–385 (1989); Hale, P. M. et al., *Internat. Immunol.* 1:409–415 (1989)). However, a potential problem with the use of any single antigenic determinant is that T cells recognize antigens in association with molecules encoded by the major histocompatibility complex (MHC) of the host, and the MHC molecules of any given individual will bind and present only a subset of potential antigenic determinants that could be recognized by the species as a whole (Benacerraf, B., *J. Immunol.* 120:1809–1812 (1978); Schwartz, R. H., *Annu. Rev. Immunol.* 3:237–261 (1985); Berzofsky, J. A., in "The Antigens". pp. 1–146, M. Sela, editor, c. 1987 by Academic Press, New York). This is true of humans as well as mice (Siliciano, R-F. et al, *Cell* 54:561–575 (1988); Schrier, R. D. et al., *J. Immunol.* 142:1166–1176 (1989); Callahan, K. M. et al, *J. Immunol.* 144:3341–3346 (1990); Martin, R. et al., *J. Immunol.* 145:540–548 (1990); Martin, R. et al.,*J. Exp. Ned.* 173:19–24 (1991); Jaraquemada, D. et al., *J. Immunol.* 145:2880–2885 (1990)).

Therefore, in order to be useful in a broad outbred population such as humans, a vaccine should contain multiple such determinants. Only limited data exist to indicate how many such determinants would have to be included. Although some concern has been raised that the number might be impractical to achieve, some data exist to suggest that as few as four such determinants could elicit responses in 85–90% of outbred humans (Clerici, M. et al., *Nature* 339:383–385 (1989)). A few antigenic peptides have been identified that appear to be promiscuous in their recognition in association with many DR molecules (sinigaglia, F. et al., *Nature* 336:778–780 (1988); Panina-Bordignon, P. et al., *Eur. J. Immunol.* 19:2237–2242 (1989)), perhaps because DR molecules share a conserved alpha chain, and in the mouse some determinants have been reported to be presented by three different I-A molecules that do not share alpha chains (Brett, S. J. et al., *J. Immunol.* 143:771–779 (1989)), or even by class II MHC molecules of different isotypes, such as I-A and I-E (Guillet, J.-G. et al., *Science* 235:865–870 (1987))). However, it is not clear how common such promiscuous epitopes are.

In the course of locating the major T-cell stimulatory sites of the HIV envelope, we observed that there were regions in the sequence that contained multiple overlapping determinants seen by mice of different MHC haplotypes (Hale, P. M. et al., *Internat. Immunol.* 1:409–415 (1989)). Although the precise determinants seen by T cells of each strain of mouse differed, each multideterminant region contained determinants that could stimulate T cells of mice of three or four of the four MHC types tested. We, therefore, reasoned that peptides encompassing such multideterminant regions might be able to stimulate T cells of many or most haplotypes of mice, and hopefully also T cells of humans of many HLA types. Thus, such multideterminant peptides might provide a means to circumvent this problem of MHC restriction in the design of synthetic vaccines. The present applicants have, therefore, tested this hypothesis by constructing six synthetic peptides of 20–33 residues each that correspond to the six multideterminant regions of HIV envelope protein localized in the mouse (Hale, P. M. et al., *Internat. Immunol.* 1:409–415 (1989)), and tested these peptides for their ability to stimulate T-cell responses in mice immunized with recombinant gp160 and in peripheral blood lymphocytes of humans infected with HIV. Although not all of the peptides were as widely recognized as expected, several such peptides were identified that were broadly recognized by both murine and human T cells of multiple H-2 and HIA types. These peptides can also immunize mice for T-cell responses to the intact HIV envelope protein, and so are useful as valuable components of a synthetic vaccine, and responses to them are useful diagnostic or prognostic markers.

SUMMARY OF THE INVENTION

It is one object of the present invention to demonstrate a process for the selection of synthetic peptides that are useful candidates for vaccines against HIV. Furthermore, a set of particular peptides are described that have demonstrated efficacy in the process above. Finally, the invention may find application in diagnostic and therapeutic settings.

DETAILED DESCRIPTION OF THE INVENTION

Figure 1A:
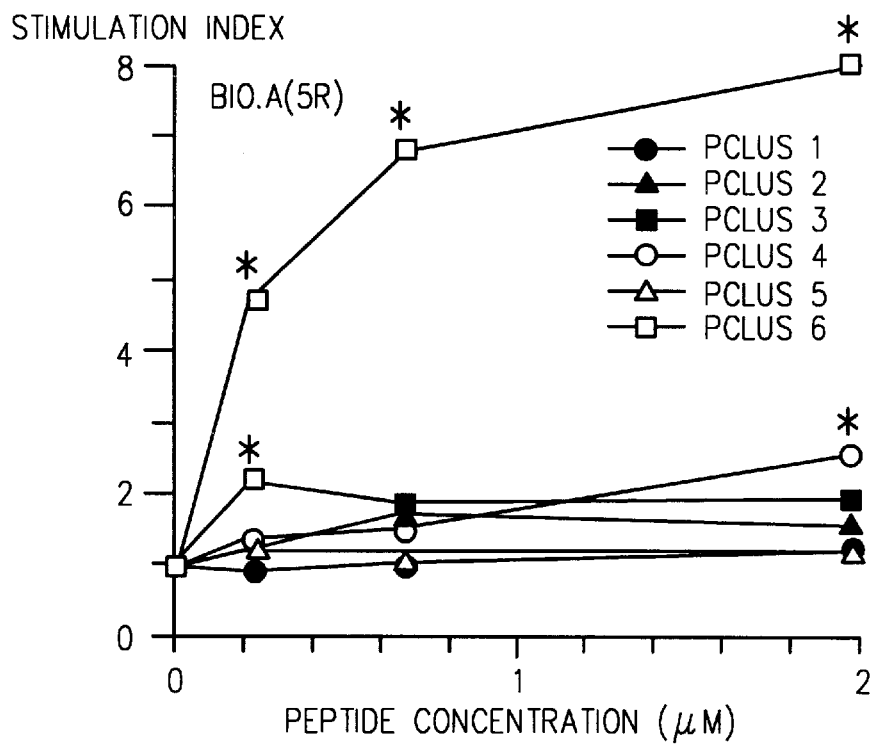
FIG. 1 shows the proliferative response of T cells from gp160-immune mice to the six cluster peptides.

The invention is described by means of several examples below. The examples are presented for purposes of illustration and are not to be construed as limiting the scope of the instant invention. It is understood that various modifications or changes in light of these examples will be suggested to persons skilled in the art and such are to be included within the spirit and purview of this application and within the scope of the appended claims.

EXAMPLE 1

Selection of peptides encompassing multideterminant clusters of HIV envelope that induce in vitro T-cell responses in mice of multiple MHC type and in a population of HIV serorositive humans 1. Synthesis of peptides The six cluster peptides are synthesized on an Applied Biosystems 430A automated peptide synthesizer using t-boc chemistry (Stewart, J. M. and J. D. Young. "Solid Phase Peptide Synthesis", Pierce Chemical Company, Rockford, Ill. (1984)). The peptides are cleaved from the resin with HF and are initially purified by molecular exclusion chromatography (P4 biogel, BioRad). Reverse phase HPLC is employed to determine degree of purity and in cases requiring further purification. The HPLC separations are carried out on Waters μbondapack reverse phase C18 analytical and preparative columns. The sequences of the peptides synthesized for the experiment are shown in Table 1 below:

TABLE 1

| Sequence of Cluster Peptides | | |
|---|---|---|
| PCLUS1 (109–128) | EQMHEDIISLWDQSLKPCVK | (SEQ ID 1) |
| PCLUS2 (324–356) | FVTIGKIGNMRQAHCNISRAKWNNTLKQIDSKL | (SEQ ID 2) |
| PCLUS3 (428–451) | KQIINMWQEVGKAMYAPPISGQIR | (SEQ ID 3) |
| PCLUS4 (483–506) | RDNWRSELYKYKVVKIEPLGVAPT | (SEQ ID 4) |
| PCLUS5 (787–820) | RIVELLGRRGWEALKYWWNLLQYWSQELKNSAVS | (SEQ ID 5) |
| PCLUS6 (828–860) | AVAEGTDRVIEVVQGAYRAIRHIPRRIRQGLER | (SEQ ID 6) |

The peptides encompassed by the six cluster peptides are shown in Table 2 below:

TABLE 2

| Sequences of Cluster Peptides and the Peptides They Encompass | |
|---|---|
| PCLUS1 (109–128) | EQMHEDIISLWDQSLKPCVK |
| HP-3 | EQMHEDIISLWDQSL |
| HP-4 | QMHEDIISLWDQSLK |
| HP-5 | HEDIISLWDQSLK |
| HP-6 | HEDIISLWDQSLR |
| HP-7 | DIISLWDQSLKPCVK |
| PCLUS2 (324–356) | FVTIGKIGNMRQAHC(NIS)RAKWNNTLKQIDSKL |
| HP-19 | FVTIGKIGNMRQAHC |
| HP-20 | RAKWNNTLKQIDSKL |
| PCLUS3 (428–451) | KQIINMWQEVGKAMYAPPISGQIR |
| HP-26 | KQIINMWQEVGKAMYA |

TABLE 2-continued

Sequences of Cluster Peptides
and the Peptides They Encompass

```
         HP-28               NMWQEVGKAMYAPPI
         HP-29                    VGKAMYAPPISGQIR

PCLUS4 (483–506)             RDNWRSELYKYKVVKIEPLGVAPT
         HP-30               RDNWRSELYKYKVVK
         HP-33                         KYKVVKIEPLGVAPT

PCLUS5 (787–820)             RIVELLGRRGWEALKYWWNLLQYWSQELKNSAVS
         HP-47               RIVELLGRRGWEALK
         HP-50                              KYWWNLLQYWSQELK
         HP-51                                   LLQYWSQELKNSAVS

PCLUS6 (828–860)             AVAEGTDRVIEVVQGAYRAIRHIPRRIRQGLER
         HP-52               AVAEGTDRVIEVVQG
         HP-53                      DRVIEVVQGAYRAIR
         HP-54                         VIEVVQGAYRAIRHI
         HP-55                              QGAYRAIRHIPRRIR
         HP-56                                     AIRHIPRRIRQGLER
```

2. Mice

B10.BR/SgSn and B10.D2/nSn strains are obtained from The Jackson Laboratory (Bar Harbor, Me., USA). B10.S (9R) and B10A(5R) strains are bred in our colony/from breeders obtained from J. Stimpfling and Jackson Laboratories, respectively.

3. gp160 preparation

Recombinant gp160 is prepared from cells infected with recombinant baculovirus expressing the gene for gp160 of the HTLV-IIIB isolate of HIV-1 as described (Javaherian, K. et al., *Proc. Natl. Acad. Sci. USA* 86:6768–6772 (1989)).

4. T-cell proliferation assay (Corradin, G., *J. Immunol.* 119:1048 (1977)). Mice are immunized subcutaneously in the tail with 20–30 μg recombinant gp160 emulsified 1:1 in complete Freund's adjuvant The mice are sacrificed 8–11 days following immunization and their draining inguinal and periaortic lymph nodes are harvested and teased into single cell suspensions in complete T-cell medium (Matis, L. A. et al., *J. Immunol.* 130:1527–1535 (1983)). Aliquots consisting of $4 \times 10^5$ cells are introduced into wells of 96-well flat-bottom culture plates containing various concentrations of the cluster peptides (2, 0.66, 0.22 μM final concentration in triplicate). After four days of incubation at 37° in 5% $CO_2$, tritiated thymidine (1 mCi) is added to all the wells. 24 hr later the cells are harvested on an automated harvesting device (Skatron) and thymidine incorporated into DNA determined by scintillation counting. The stimulation index is the ratio of cpm incorporated in the presence of antigen to cpm incorporated by cells cultured with medium alone.

Each cluster peptide of Table 1 was synthesized and purified as described above and tested for the ability to stimulate T-cell proliferative responses of mice of the four MHC types noted that had been immunized with recombinant gp160. B10 congenic mice are used that differed only in their MHC type, but are otherwise genetically identical. The four mouse MHC types studied are chosen because they represent four independent MHC haplotypes that each express both an I-A and an I-E molecule, and differ from each other in both of these molecules. Thus the four strains together express eight different murine class II MHC molecules. It should be noted that the murine I-E molecules, like human DR molecules to which they are homologous, all share a conserved alpha chain, but differ in their beta chain, which accounts for all the polymorphism. Responses to most antigens differ among the several I-E and DR alleles, indicating the important role of the beta chain, despite the shared alpha chain.

Figure 1B:
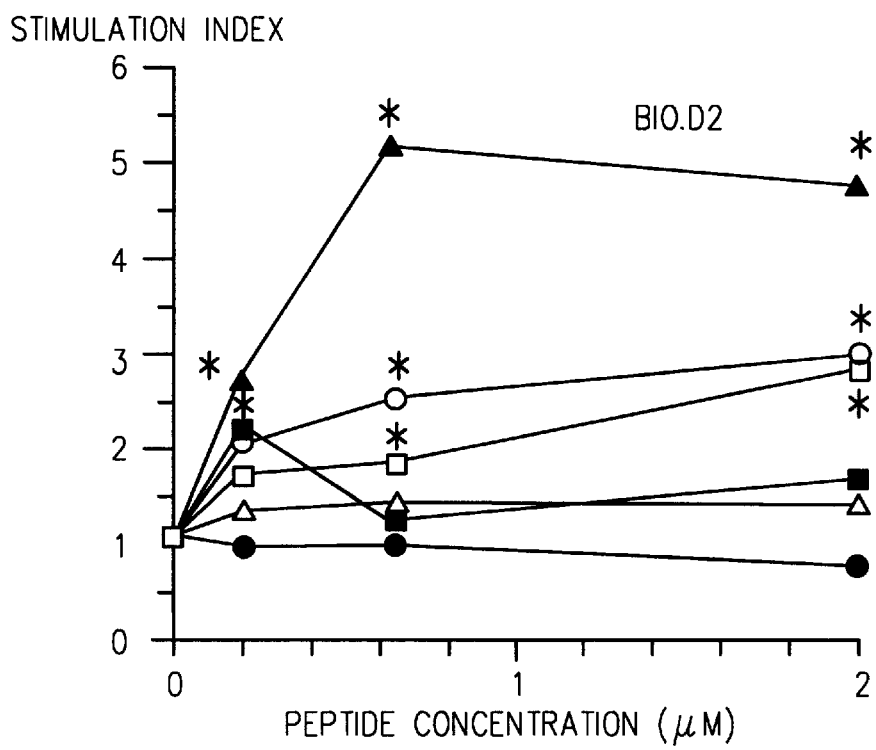
Figure 1C:
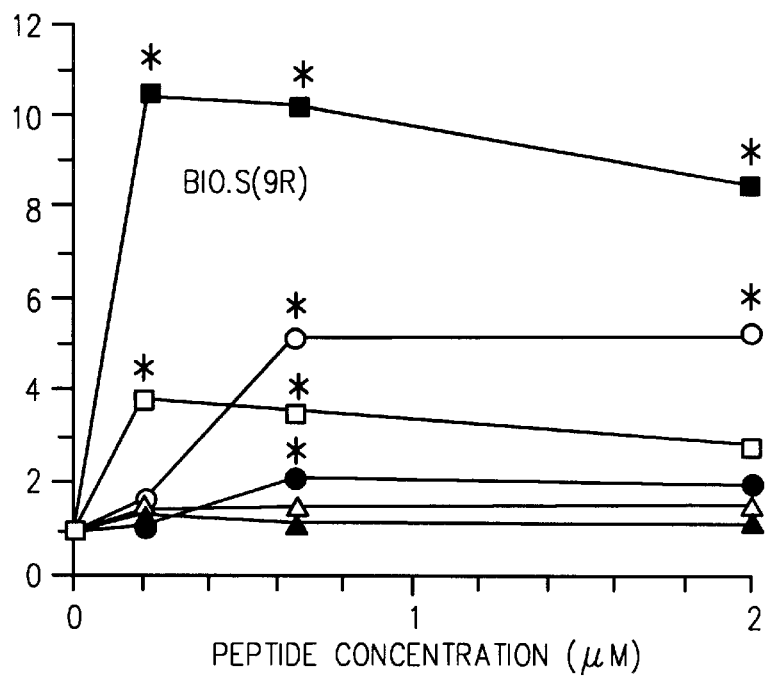
Figure 1D:
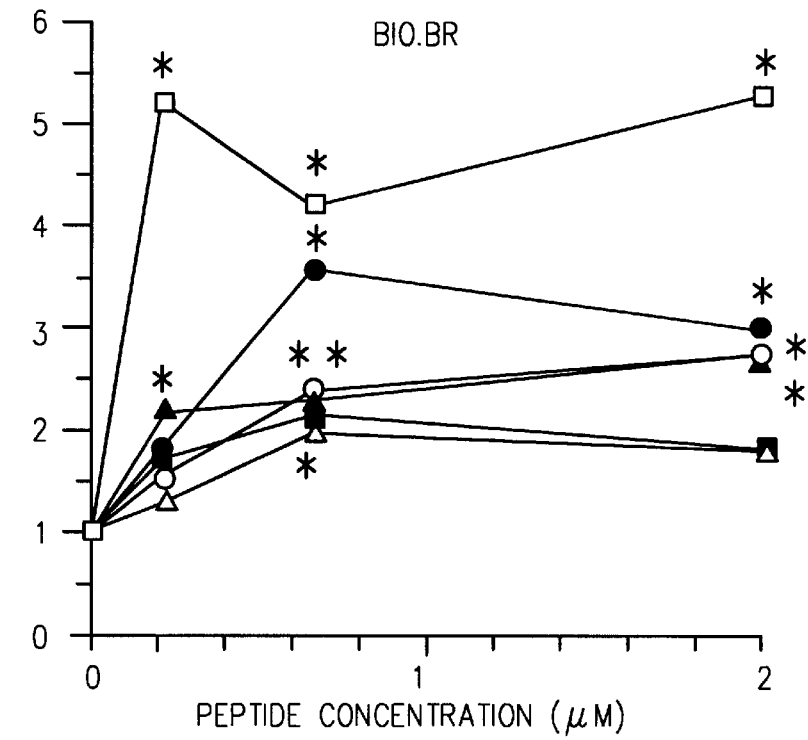
Figure 2A:
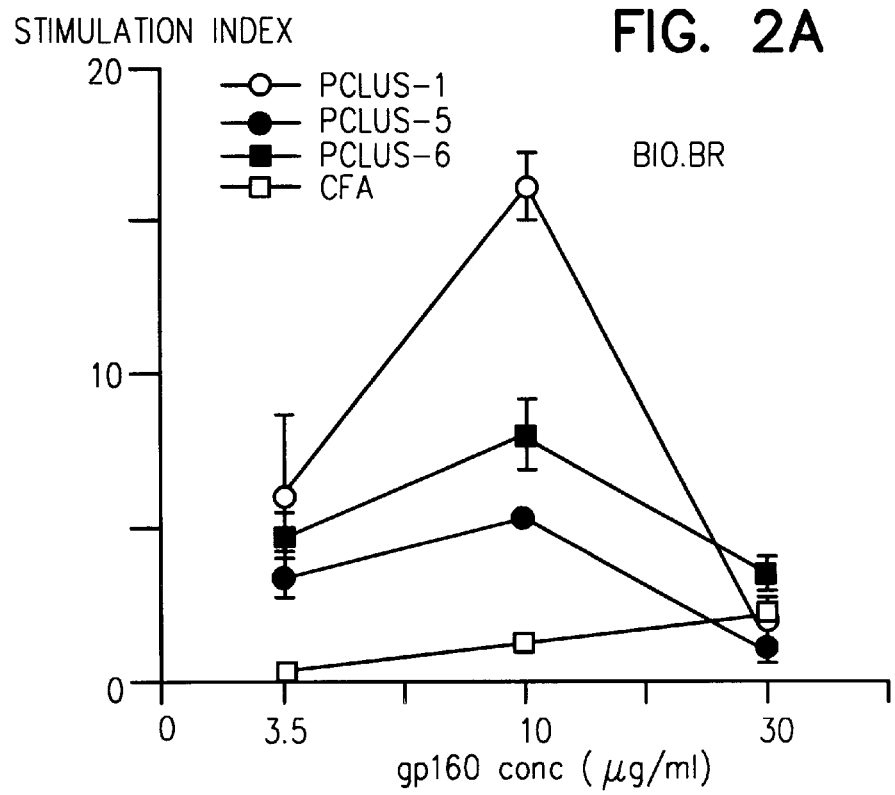
FIG. 2 shows the proliferation response to recombinant gp160 of T-cells isolated from the lymph nodes of mice immunized with cluster peptides.
Figure 2B:
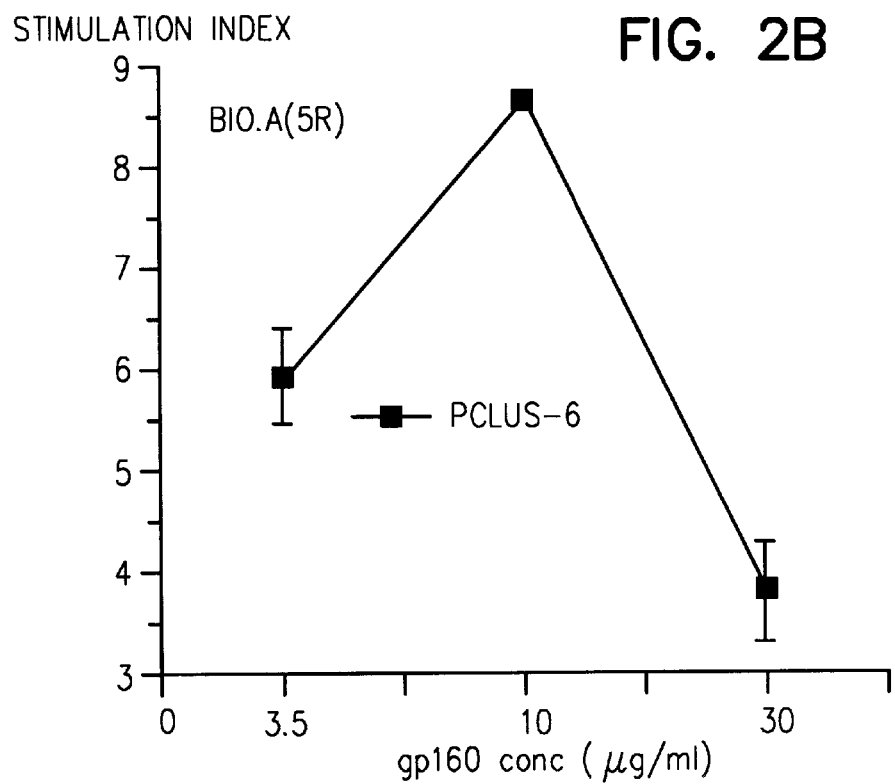
Figure 2C:
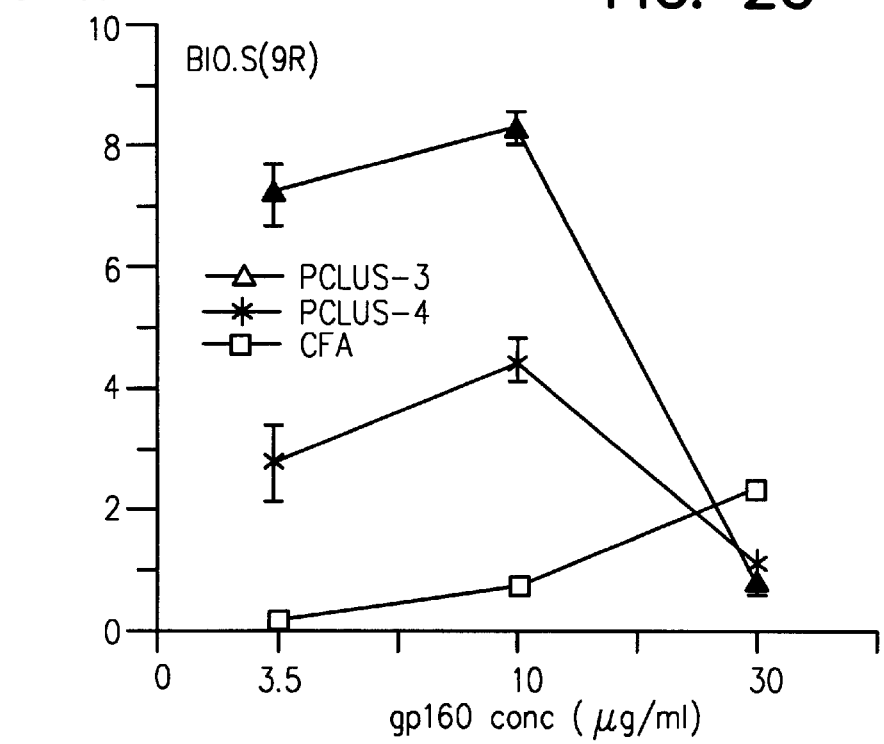
Figure 2D:
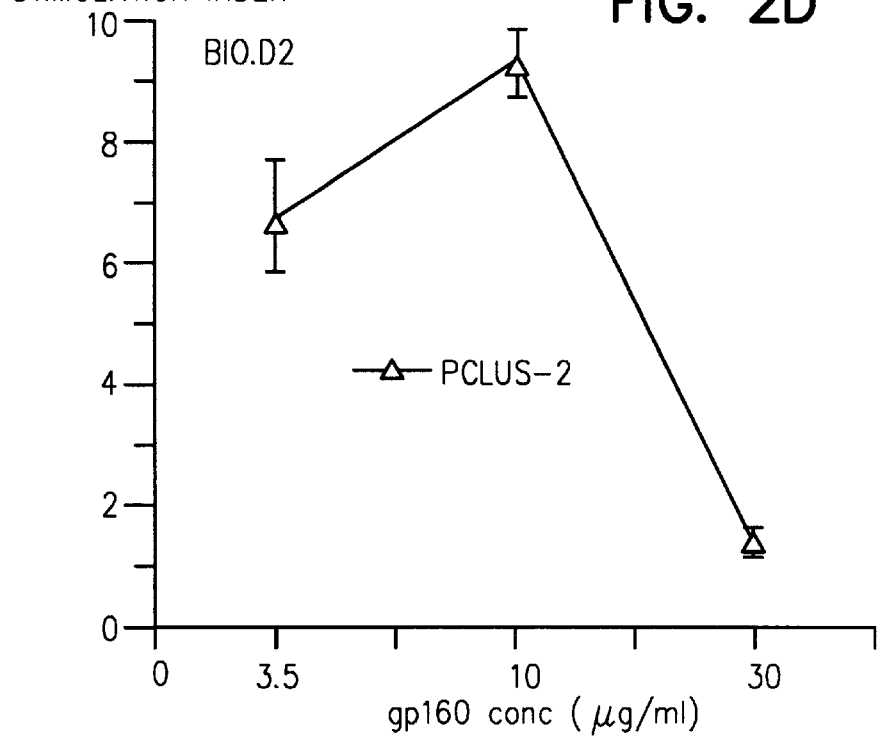

Each peptide was studied in four independent experiments (or three for cluster peptide 3, which was synthesized last), and the results pooled by determining the geometric mean of the stimulation indices for a given peptide concentration in all four experiments. The results are presented in FIG. 1, which shows the stimulation index as a function of peptide concentration in the culture, for 4 congenic strains of mice representing 4 distinct MHC haplotypes. Each value is the geometric mean stimulation index of 4 (or 3 in the case of cluster peptide 3) independent experiments. Although the results of the several experiments were qualitatively similar, the absolute values of the stimulation indices varied sufficiently as to make error bars difficult to read on these plots. Instead, values for which the mean stimulation index of all experiments is statistically significantly different from background (1.0) as measured by a Student's t test ($p<0.05$) are indicated with an asterisk. Results were considered positive only if this statistic was significant and the mean stimulation index of all experiments was >2. Cluster peptides 3, 4 and 6 were the only ones to elicit a positive response in mice of all four MHC haplotypes. Cluster peptide 6 stimulated most strongly in B10.BR and B10.A(5R) mice, and gave weaker but significantly positive and reproducible responses in B10.S(9R) and B10.D2. Cluster peptide 4 stimulated most strongly in B10.S(9R), but was significantly and reproducibly positive in the other strains as well. Cluster peptide 3 stimulated very strongly in B10.S(9R), and gave weak but statistically significant responses in the other three strains. The responses were more strongly positive in some experiments for these other strains, but some variability in magnitude of response reduced the geometric mean, although they remained statistically significant. These three peptides thus fulfill the predictions of the hypothesis (Hale, P. M. et al., *Internat. Immunol.* 1:409–415 (1989)) that by making an extended peptide encompassing overlapping antigenic determinants recognized by mice of multiple haplotypes, the resulting construct would be broadly recognized by all or most haplotypes.

The remaining three peptides elicited responses in fewer strains of mice than expected. Cluster peptide 2 was strongly positive in only two strains, B10.D2 and B10.BR, despite the fact that all four strains had recognized at least one site encompassed within this multideterminant region in our earlier study (Hale, P. M. et al., *Internat. Immunol.* 1:409–415 (1989)). Similarly, cluster peptide 1 was recognized by one strain, B10.BR, strongly, and by another strain, B10.S(9R) only marginally, despite the fact that all four strains had recognized components of this multideterminant region. The most disappointing peptide was cluster peptide 5, which failed to elicit a significant response in three strains, and gave only a marginal response in the fourth strain BIO.BR. These results suggest that the larger peptide is not simply the sum of its parts, but may fail to stimulate in strains that a smaller subcomponent would stimulate, perhaps because parts of the larger structure hinder interaction with MHC or T cell receptor, or because they cause the peptide to fold back on itself (Brett, S. J. et al., *J. Exp. Med.* 168:357–373 (1988); Gammon, G. et al., *Immunol. Rev.* 98:53–73 (1987); Vacchio, M. S. et al., *J. Immunol.* 143:2814–2819 (1989); Berzofsky, J. A. et al., *Immunol. Rev.* 106:5–31 (1988)) or because of different processing requirements.

5. IL-2 production by human PBL. For the assay of antigen-induced IL-2 production by human peripheral blood T cells, PBL from HIV-seropositive asymptomatic blood donors are separated on lymphocyte separation medium (LSM, Organon Teknika Corp, Durham, N.C.), washed twice, counted, and resuspended at $3 \times 10^6$/ml in RPMI 1640 (Gibco, Grand Island, N.Y.) containing 50 U/ml penicillin and 2 mM glutamine. In triplicate wells in a 96-well flat bottom plate (Costar, Cambridge, Mass.), 0.1 ml of PBL is added per well and cultured without stimulation or stimulated with: a) influenza A/Bangkok RX73 (final dilution 1:1000); b) PHA (Gibco) (antigen dilution 1:100); or c) cluster peptides at a final concentration of 2.5 $\mu$M. Pooled AB+ plasma is added to each well (final dilution 1:20). The anti-IL-2 receptor antibody anti-Tac (obtained from Dr. T. A. Waldmann, NCI) is added to each well at the initiation of culture (final concentration 5 $\mu$M) in order to block IL-2 consumption. The supernatants of the cell cultures are harvested 7 d later and frozen at –20° C. The supernatant IL-2 activity is assessed as the ability to stimulate the proliferation of the IL-2-dependent CTLL cell line as previously described (Clerici, M. et al., *J. Clin. Invest.* 84:1892–1899 (1989)).

Although prior publications demonstrate that many peptides that elicit responses in murine T cells also do so with human T cells (Berzofsky, J. A. et al., *Nature* 334:706–708 (1988); Clerici, M. et al, *Nature* 339:383–385 (1989); Lamb, J. R. et al., *Nature* 300:66–69 (1982); Hurwitz, J. L. et al., *J. Immunol.* 133:3371–3377 (1984); Good, M. F. et al., *Science* 235:1059–1062 (1987); Good, M. F., *Proc. Natl. Acad. Sci. USA* 85:1199–1203 (1988)); Dontfraid, F. et al., *Mol. Biol. Med.* 5:185–196 (1988)), there were no data on human T cells to some of the components of the cluster peptides. Therefore, the experiments leading to the present invention were designed to test the hypothesis that peptides that elicit responses in mice of multiple MHC types were likely to elicit responses in humans of multiple HLA types as well. It was known from earlier work that peptide envT2 (residues 112–124) contained within cluster peptide 1, peptide envT1 (residues 428–443) contained within cluster peptide 3, and peptide TH4.1 (residues 834–848, also known as HP53) contained within cluster peptide 6 all stimulated responses in 50–67% of HIV-infected human subjects who could still respond to positive-control recall antigens such as influenza A virus (flu) or tetanus toxoid (Clerici, M. et al., *Nature* 339:383–385 (1989)). However, we had no prior experience with peptides from these other multideterminant regions in humans. Because the proliferative and IL-2 productive responses to soluble protein antigens is lost early in HIV infection, frequently when patients are still asymptomatic and have normal CD4+ cell numbers (Clerici, M. et al., *Nature* 339:383–385 (1989); Clerici, M. et al., *J. Clin. Invest.* 84:1892–1899 (1989); Lane, H. C. et al., *New Engl. J. Med.* 313:79–84 (1985)), responses to flu and tetanus toxoid were used as positive controls in these experiments to exclude donors unresponsive to all such recall protein antigens.

All six cluster peptides were tested for the ability to stimulate IL-2 production by peripheral blood T cells from a series of HIV-seropositive but asymptomatic volunteers, as well as HIV-seronegative controls. All 15 seronegative controls responded to the control recall antigen influenza virus (flu), but only 42 of the 59 HIV-seropositive donors responded to flu. Because of our previous experience that seropositive donors who fail to respond to control recall protein antigens such as flu or tetanus toxoid also fail to respond to HIV peptides (Clerici, M. et al., *Nature* 339:383–385 (1989)), the 17 donors who failed to respond to flu were excluded from further study. Because some of the peptides had not been purified at the time some of the donors were available, these peptides were tested on cells from a subset of the donors. Results for the six cluster peptides in the 42 HIV-seropositive flu-positive donors and 15 control HIV-seronegative donors are given in Table 3, and summarized in Table 4.

TABLE 3

IL-2 Production by T cells from HIV-seropositive and seronegative human blood donors

| Donor Number | FLU | Cluster Peptide Number | | | | | |
|---|---|---|---|---|---|---|---|
| | | 1 | 2 | 3 | 4 | 5 | 6 |
| HIV+ Donors | | | | | | | |
| 317 | 64.5 | 11.4(NS) | 1.9 | NT | NT | NT | 29.7 |
| 453 | 91.4 | 5.0(NS) | 30.2 | NT | NT | NT | 16.3 |
| 909 | 6.3 | 7.8 | 9.1 | NT | NT | NT | 9.4 |
| 360 | 4.0 | 2.7 | 2.2 | NT | 2.3 | 2.8 | 3.3 |
| 396 | 3.2 | 2.4 | 1.7 | NT | 2.2 | 7.5 | 3.1 |
| 131 | 8.2 | 2.8 | 5.7 | NT | 1.4 | 2.3 | 5.2 |
| 208 | 5.1 | .5 | 1.9 | NT | 1.2 | .1 | .4 |
| 335 | 26.4 | 9.2 | 9.0 | NT | 9.0 | 9.4 | 6.4 |
| 69 | 3.6 | 2.3 | 4.7 | NT | .2 | 2.4 | 1.6 |
| 556 | 3.4 | 4.0 | .8 | NT | 1.0 | 2.1 | 1.5 |
| 212 | 37.9 | 21.9 | 13.1 | NT | .8 | .8 | 1.2 |
| 375 | 15.1 | 6.1 | .8 | NT | .2 | .2 | 5.7 |
| 564 | 7.8 | 4.8 | 4.1 | NT | 1.7 | 2.8 | 2.9 |
| 83 | 26.5 | 2.7 | 13.3 | NT | 8.4 | 1.8 | 1.0 |
| 621 | 112.3 | 54.8 | 39.1 | NT | .6 | 36.3 | 14.4 |
| 920 | 5.5 | 2.1 | 1.7 | NT | .5 | 1.3 | 2.2(NS) |
| 90 | 16.0 | 2.4 | 4.4 | 2.9 | 7.0 | 4.2 | 1.5 |
| 224 | 3.1 | 1.3 | 1.4 | NT | 3.2 | 1.6 | 1.0 |
| 430 | 7.9 | 3.1 | 2.8 | NT | 1.3 | 2.5 | 3.0 |
| 698 | 6.5 | 2.6 | 4.7 | NT | 3.4 | 4.6 | 4.4 |
| 399 | 6.7 | 1.7 | 1.4 | NT | 1.0 | 1.3 | 1.2 |
| 923 | 7.9 | 2.4 | 1.6 | NT | 1.4 | 2.8 | 3.0 |
| 75 | 14.2 | .8 | 5.4 | 4.8 | .4 | 3.6 | 5.0 |
| 281 | 16.1 | 5.9 | 1.1 | NT | 3.3 | 7.9 | 1.1 |
| 357 | 26.1 | 2.0(NS) | 5.8 | NT | 12.2 | 6.3 | 5.1 |
| 395 | 36.7 | 4.1 | 7.9 | NT | 11.3 | 2.3(NS) | 7.0 |
| 916 | 36.2 | 12.0 | 2.7 | NT | 3.8 | 11.7 | 5.8 |
| 232 | 7.5 | 2.1(NS) | .3 | NT | NT | NT | 1.9 |
| 755 | 8.6 | .5 | .2 | NT | NT | NT | 1.8 |
| 193 | 22.3 | 1.4 | 13.2 | NT | NT | NT | 54.9 |
| 911 | 15.8 | 2.1 | 3.1 | NT | NT | NT | 3.1 |
| 419 | 12.9 | .9 | 6.6 | NT | NT | .9 | 1.7 |
| 914 | 9.3 | .4 | .5 | NT | NT | .3 | .5 |
| 132 | 18.9 | 1.8 | 1.4 | 1.5 | 4.9 | 1.4 | NT |
| 504 | 20.4 | 5.3 | 13.8 | 9.6 | 13.8 | 9.1 | NT |
| 933 | 17.7 | 9.6 | 1.4 | 7.7 | 9.7 | .3 | NT |
| 213 | 6.8 | NT | NT | 0.5 | NT | NT | NT |
| 421 | 12.7 | NT | NT | 10.9 | NT | NT | NT |

TABLE 3-continued

IL-2 Production by T cells from HIV-seropositive and seronegative human blood donors

| Donor Number | FLU | Cluster Peptide Number | | | | | |
|---|---|---|---|---|---|---|---|
| | | 1 | 2 | 3 | 4 | 5 | 6 |
| 604 | 6.1 | NT | NT | 1.7 | NT | NT | NT |
| 851 | 5.6 | NT | NT | 8.9 | NT | NT | NT |
| 904 | 22.5 | NT | NT | 8.1 | NT | NT | NT |
| 906 | 3.1 | NT | NT | 5.7 | NT | NT | NT |
| HIV-CONTROLS | | | | | | | |
| HC1 | 6.6 | .8 | 1.0 | NT | NT | NT | 3.1 |
| HC2 | 8.4 | .2 | .4 | NT | 2.5 | .2 | .1 |
| HC3 | 2.9 | .3 | .7 | NT | .4 | .3 | .6 |
| HC4 | 7.3 | 1.0 | .9 | NT | .1 | .7 | 1.1 |
| HC5 | 10.9 | .6 | 2.2 | NT | .5 | .2 | 1.9 |
| HC6 | 7.0 | .7 | .5 | 1.0 | NT | .3 | .7 |
| HC7 | 3.9 | 1.8 | .9 | .8 | NT | 1.1 | 1.0 |
| HC8 | 4.4 | .9 | .8 | .2 | NT | 1.4 | .7 |
| HC12 | 6.2 | .7 | .2 | .9 | .1 | .1 | NT |
| HCbb1 | 6.3 | .7 | .7 | .4 | 1.0 | .5 | NT |
| HCbb2 | 17.6 | .2 | .4 | .2 | .7 | .6 | .4 |
| HCbb3 | 5.5 | .6 | .1 | .2 | .1 | .4 | .4 |
| HCbb4 | 74.6 | 1.3 | 1.9 | .9 | .7 | .8 | .5 |
| HCbb5 | 6.7 | 2.9 | 15.3 | 1.2 | .2 | .5 | .7 |
| HCbb6 | 6.5 | 1.1 | .8 | 1.2 | 1.2 | 1.8 | NT |

Values shown are stimulation indices for proliferation of an IL-2-dependent CTLL cell line in the presence of a 1:2 dilution of culture supernatant from triplicate cultures of PBL from the indicated donor with a 2.5 μM concentration of the indicated peptide, as described above. All of the seropositive donors and controls studied were responsive to the positive control recall protein antigen flu. For a value to be considered positive, it had to simultaneously meet two criteria: The replicates had to be statistically significantly different from the control replicates for that donor by Student's t test ($p<0.05$), and the stimulation index had to be greater than twice the medium control. Six cases marked NS were stimulation indices >2.0 which were not counted as positives because the replicates were not statistically significant. In several cases with SI<2.0, the replicates were significantly different from background, but these were not considered positive because of the low stimulation index. The requirement for both criteria is thus more conservative than using either alone.

TABLE 4

Summary of Human T-cell IL-2 Responses to Cluster Peptides

| | Cluster Peptide 1 | Cluster Peptide 2 | Cluster Peptide 3 | Cluster Peptide 4 | Cluster Peptide 5 | Cluster Peptide 6 |
|---|---|---|---|---|---|---|
| HIV + FLU + 19/33 Donors | 23/36 | 21/36 | 8/11 | 14/27 | 17/29 | |
| | 64% | 58% | 73% | 52% | 59% | 58% |
| HIV-FLU + 1/12 Controls | 1/15 | 2/15 | 0/10 | 1/11 | 0/14 | |
| | 7% | 13% | 0% | 9% | 0% | 8% |

See legend to table 3 for criteria for positivity.

TABLE 5

HLA Typing of HIV-seropositive donors

| Donor | HLA-A | HLA-B | HLA-C | DQ | DR |
|---|---|---|---|---|---|
| 90 | 24, 29 | 7, 44 | 2, 3 | | |
| 208 | 9 (23), 32 | 7, 17 | 3 | 1, 2 | 2, 3 |
| 281 | 23, 33 | 17 | 3 | 2 | 1, 3 |
| 375 | 2, 24 | 35, 61 | 2, 4 | 1 | 3 |
| 131 | 1, 3 | 7, 62 | 3 | 1, 3 | 2, 4 |
| 909 | 30, 33 | 17 | 3 | 1 | 1, 2 |
| 232 | 9, 31 | 14, 18 | 3 | 2, 3 | 3, 5 |
| 755 | 2, 28 | 35, 15 | 2, 3 | 1, 3 | 2, 4 |
| 75 | 30 | 7, 18 | 2 | | |
| 360 | 2, 31 | 51 | 2 | | |
| 317 | 28 | 12 | 3 | 1, 2 | 2, 4 |
| 395 | 1, 3 | 7, 8 | — | | |

All six cluster peptides stimulated IL-2 production in more than half of the HIV-seropositive, flu-positive donors. Cluster peptides 1 and 3 were most broadly recognized, giving responses in 64% and 73% of the donors. Cluster peptides 2, 5, and 6 were close seconds, positive in 58, 59, and 58% of the donors, respectively. The least broadly recognized was cluster peptide 4, but even this stimulated 52% of the donors. In contrast, none or only one of the control seronegative donors responded to any of the peptides except cluster peptide 2, which stimulated 2 of the 15 control donors (13%). Thus, none of the peptides was nonspecifically mitogenic. The human donors were unrelated Air Force personnel, originally from different parts of the United States, and of diverse HLA types. Because of limited availability of blood, only 13 of the HIV+ donors could be HIA-typed, and only 8 could be typed for DR and DQ, which require more blood (Table 5). In this limited sample, no correlation between response to any peptide and any HLA type could be detected. We conclude that all of these cluster peptides fulfill the hypothesis that peptides which are broadly recognized by murine T cells are likely to be broadly recognized by human T cells as well. Indeed, some of the peptides, such as cluster peptides 1 and 5, were more broadly recognized by humans of diverse HLA types than by different strains of inbred mice tested.

The results in Table 3 indicate that 31 (86%) of the 36 donors responsive to the positive control antigen flu who were tested with at least three peptides responded to at least one of them. To further test the extent of the population that could respond, an additional 13 HIV-seropositive donors responsive to flu, not overlapping with the donors listed in Table 3, were tested for their response to a mixture of the six cluster peptides, each at 2.5 μM. Ten of these 13, or about 77%, responded, whereas none of four seronegative donors responded to the mixture of peptides, although all four responded to flu. Although it is possible that the peptides in the mixture may compete with each other for binding to some MHC molecules, given the small sample sizes in the two groups studied, there is probably not a statistically significant difference between the fraction responding to at least one peptide in the first group and the fraction responding to the mixture in the second. In either case, we conclude that a sizable majority of people are capable of making T cell responses to these peptides.

6. Immunization with peptides to induce T cells responding to intact gp160 in vitro.

If the peptides identified by the two screening techniques above are to be useful components of a vaccine, it is important that they not only be recognized by T-cells immune to the HIV envelope protein gp160, but also that they be immunogenic to elicit T cells in vivo that can respond to gp160. Of course, the immunizations cannot be performed yet in the clinically relevant species, (uninfected) humans, but it is desirable to be sure that for the strains of mice shown above to have T cells responsive to these peptides, the mice can be immunized in vivo with the peptides and elicit T cells that respond to intact gp160 in vitro. Each peptide is tested by immunizing mice of the strain responding best to that peptide based on the data in FIG. 1. Mice of the four strains shown are immunized subcutaneously in the tail with 8–10 nmoles of the indicated cluster peptide in a 1:1 emulsion with CFA, final volume per mouse 50 $\mu$l except for cluster peptide 2 which was in 75 $\mu$l. Twelve days later, the draining lymph nodes are harvested from 2 mice of each group (strain and peptide combination) and assayed as described above. Results are shown as stimulation indices, the ratio of experimental cpm over cpm from stimulation with medium alone, which ranged from 3000–7000 cpm for the different groups.

B10.BR mice immunized with cluster peptide 1, cluster peptide 5, or cluster peptide 6 all produced T cells that could be stimulated by recombinant gp160 in vitro (FIG. 2, panel A). As a control for possible mitogenicity of the recombinant gp160, T cells from B10.BR mice immunized with only complete Freunds adjuvant did not respond significantly to the gp160 in vitro (FIG. 2, panel A). Therefore, the in vitro response was a result of immunization with the peptides. Similarly, T cells from B10.S(9R) mice immunized with either cluster peptide 3 or cluster peptide 4 responded to recombinant gp160 in vitro, whereas similar mice immunized with adjuvant alone made a weak (mitogenic) response at only the highest concentration (FIG. 2, panel B). Likewise, BIO.A(5R) mice immunized with cluster peptide 6 and B10.D2 mice immunized with cluster peptide 2 produced T cells responsive to gp160 in vitro (FIG. 2, panels C and D). All of these responses show high dose inhibition typical of T-cell proliferative responses, but in this case the decreased response at 30 $\mu$g/ml also may be due to some toxicity of the recombinant gp160 preparation, which was solubilized in 8M urea and sodium dodecyl sulfate. Although the gp160 was dialyzed before use, it is possible that residual detergent that is hard to remove was toxic at the highest dose. Nevertheless, the clear response at 10 $\mu$g/ml in all cases indicates that all six cluster peptides elicit in vivo T cells that can react with gp160.

EXAMPLE 2

Use of cluster peptides in a diagnostic assay for HIV-1 infection of patients

The cluster peptides described in Table 1 above may be utilized for the diagnosis of HIV-1 exposure infection in patients. The detection of HIV-1 gp160 specific T cell responses to these peptides can be accomplished by standard techniques of T-cell proliferation and production of IL-2 or other lymphokines as described above in Example 1, items 4 and 5, applied to humans as described in Clerici et al., Nature, Vol. 339, pp. 383–385 (1989).

Alternatively, the diagnostic test can be of a cytotoxicity format as described for the peptide env-$K_1$ in Berzofsky, et al., U.S. patent application Ser. No. 07/148,692. This format has the advantage of detecting infected individuals that are not yet producing antibodies to HIV.

EXAMPLE 3

Chemical modification of the cluster peptides to enhance their pharmacologic characteristics Small peptides circulating in the blood are subject to degradation by proteolytic action and clearing by the kidneys. Yet, a number of naturally occurring peptides are found in the circulation, for example the enkephalins. These small peptides are often found to be modified by amidation of the carboxy-terminus (Kitamura, K. et al., *Biochem. Biophys. Res. Comm.* 169:1164–1171 (1990); Dickson, C. J. and Yamada, T., *J. Biol. Chem.* 266:334–338 (1991)). Thus, it may prove advantageous to produce chemically modified variants of the cluster peptides for use in therapeutic applications. The enzymatic carboxy-terminal amidation of a synthetic peptide has been described (Suzuki, K. et al., *EMBO J.* 9:4259–4265 (1990); Katopodis, G. A. et al., *Biochemistry* 30:6189–6194 (1991)). Also, the addition of residues useful for the cross-linking of the peptides to carrier proteins for immunizations or to solid supports for immunoassay or antibody purification applications may prove advantageous. Many means for chemical modification of peptides are well known in the art.

The peptides of the instant invention could also be coupled to, or co-synthesized with, peptides that bind to or induce production of neutralizing antibodies to HIV or cytotoxic T-cells specific for HIV. Thus, a peptide of the present invention can be coupled, by chemical coupling or co-synthesis, to a second peptide containing a T-cell or B-cell epitope. The peptides of the instant invention serve as HIV T-specific carriers in such constructs, which advantageously induce a memory in T-cells which would cause a memory helper T-cell response on exposure to HIV, in contrast to the use of HIV-unrelated carriers which would not produce such a memory response on exposure to the virus. Methods for coupling or cosynthesizing peptides with specific carriers are, for example; as described in Good, M. F. et al., *Science, Vol.* 235, pp. 1059–1062 (1987); U.S. Pat. No. 4,886,782 to Good et al.; and Palker, T. J. et al., J. of Immunology, Vol. 142, pp. 3612–3619 (1989), which are hereby incorporated by reference.

EXAMPLE 4

Administration of cluster peptides as a vaccine against HIV-1

The aim of the research of a large number of biomedical researchers is the production of a vaccine which would produce protection to humans from infection by HIV-1 or therapeutic benefit in AIDS treatment. The instant invention provides a means for identifying peptides that may prove useful as such vaccines as well as specifying six particular peptides as candidates based on the production of a T-cell response to the protein target from which the peptides are derived in mice immunized with the peptide. A pharmaceutical composition including a vaccine in accordance with the present invention comprises an effective antigenic or therapeutic amount of at least one of the cluster peptides and a pharmaceutically acceptable carrier such as physiological saline, non-toxic, sterile buffer and the like. Of course, additives such as preservatives, sterilants, adjuvants and the like, well known to one of ordinary skill in the art, could also be included in the pharmaceutical composition to maintain or increase the efficacy of the preparation.

It is proposed that peptides of the instant invention can also be administered as a vaccine in a fashion similar to that for the administration to primates of a synthetic peptide vaccine against hepatitus B as described by Itoh (Itoh, Y. et al., *Proc. Natl. Acad. Sci. USA* 83:9174–9178 (1986)). An alternative method for the preparation of vaccines involves the use of Protein A coated microbeads that bind immune complexes of an antibody and the immunizing antigen on their outer surface described for example in Platt, et al., U.S. Pat. No. 4,493,825, hereby incorporated by reference. In addition, the cluster peptides of the invention could be coupled to, or conjugated with, peptides that bind to or induce production of neutralizing antibodies to HIV or cytotoxic T cells to HIV.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

SEQUENCE LISTING

```
(1) GENERAL INFORMATION:

(iii) NUMBER OF SEQUENCES: 6

(2) INFORMATION FOR SEQ ID NO:1:

(i) SEQUENCE CHARACTERISTICS:
          (A) LENGTH: 20 amino acids
          (B) TYPE: amino acid
          (D) TOPOLOGY: linear (ii) MOLECULE TYPE: protein (v) FRAGMENT TYPE: internal (vi) ORIGINAL SOURCE:
          (A) ORGANISM: HIV-1

(ix) FEATURE:
          (A) NAME/KEY: Peptide
          (B) LOCATION: 1..20
          (D) OTHER INFORMATION: /label= peptide
               /note= "synthetic peptide fragment of HIV-1 gp160"

(ix) FEATURE:
          (A) NAME/KEY: Peptide
          (B) LOCATION: 1..15
          (D) OTHER INFORMATION: /label= peptide
               /note= "peptide hp-3 of table 2"

(ix) FEATURE:
          (A) NAME/KEY: Peptide
          (B) LOCATION: 2..16
          (D) OTHER INFORMATION: /label= peptide
               /note= "peptide hp-4 of table 2"

(ix) FEATURE:
          (A) NAME/KEY: Peptide
          (B) LOCATION: 4..16
          (D) OTHER INFORMATION: /label= peptide
               /note= "peptide hp-5 of table 2"

(ix) FEATURE:
          (A) NAME/KEY: Peptide
          (B) LOCATION: 4..16
          (D) OTHER INFORMATION: /label= peptide
               /note= "peptide hp-6 in table 2.  in this peptide
               residue 16 is changed from lysine to arginine."

(ix) FEATURE:
          (A) NAME/KEY: Peptide
          (B) LOCATION: 6..20
          (D) OTHER INFORMATION: /label= peptide
               /note= "peptide hp-7 of table 2"

(x) PUBLICATION INFORMATION:
          (H) DOCUMENT NUMBER: US 5,030,449
          (I) FILING DATE: 21-JUL-1988
          (J) PUBLICATION DATE: 09-JUL-1991
          (K) RELEVANT RESIDUES IN SEQ ID NO:1: FROM 1 TO 20

(x) PUBLICATION INFORMATION:
          (H) DOCUMENT NUMBER: US 07/148,692
          (I) FILING DATE: 26-JAN-1988
          (K) RELEVANT RESIDUES IN SEQ ID NO:1: FROM 1 TO 20

(xi) SEQUENCE DESCRIPTION: SEQ ID NO:1:

Glu Gln Met His Glu Asp Ile Ile Ser Leu Trp Asp Gln Ser Leu Lys
```

```
1               5                  10                 15
Pro Cys Val Lys
             20

(2) INFORMATION FOR SEQ ID NO:2:

(i) SEQUENCE CHARACTERISTICS:
        (A) LENGTH: 33 amino acids
        (B) TYPE: amino acid
        (D) TOPOLOGY: linear (ii) MOLECULE TYPE: protein (v) FRAGMENT TYPE: internal (vi) ORIGINAL SOURCE:
        (A) ORGANISM: HIV-1

(ix) FEATURE:
        (A) NAME/KEY: Peptide
        (B) LOCATION: 1..31
        (D) OTHER INFORMATION: /label= peptide
              /note= "synthetic fragment of HIV-1 gp160"

(ix) FEATURE:
        (A) NAME/KEY: Peptide
        (B) LOCATION: 1..15
        (D) OTHER INFORMATION: /label= peptide
              /note= "peptide hp-19 of table 2"

(ix) FEATURE:
        (A) NAME/KEY: Peptide
        (B) LOCATION: 18..31
        (D) OTHER INFORMATION: /label= peptide
              /note= "peptide hp-20 of table 2"

(x) PUBLICATION INFORMATION:
        (H) DOCUMENT NUMBER: US 5,030,449
        (I) FILING DATE: 21-JUL-1988
        (J) PUBLICATION DATE: 09-JUL-1991
        (K) RELEVANT RESIDUES IN SEQ ID NO:2: FROM 1 TO 20

(x) PUBLICATION INFORMATION:
        (H) DOCUMENT NUMBER: US 07/148,692
        (I) FILING DATE: 26-JAN-1988
        (K) RELEVANT RESIDUES IN SEQ ID NO:2: FROM 1 TO 20

(xi) SEQUENCE DESCRIPTION: SEQ ID NO:2:

Phe Val Thr Ile Gly Lys Thr Gly Asn Met Arg Gln Ala His Cys Asn
1               5                  10                 15

Ile Ser Arg Ala Lys Trp Asn Asn Thr Leu Lys Gln Ile Asp Ser Lys
             20                  25                 30

Leu (2) INFORMATION FOR SEQ ID NO:3:

(i) SEQUENCE CHARACTERISTICS:
        (A) LENGTH: 24 amino acids
        (B) TYPE: amino acid
        (D) TOPOLOGY: linear (ii) MOLECULE TYPE: protein (v) FRAGMENT TYPE: internal (vi) ORIGINAL SOURCE:
        (A) ORGANISM: HIV-1

(ix) FEATURE:
        (A) NAME/KEY: Peptide
        (B) LOCATION: 1..25
        (D) OTHER INFORMATION: /label= peptide
              /note= "synthetic peptide fragment of HIV-1 gp160"
```

```
        (ix) FEATURE:
              (A) NAME/KEY: Peptide
              (B) LOCATION: 1..16
              (D) OTHER INFORMATION: /label= peptide
                    /note= "peptide hp-26 in table 2"

(ix) FEATURE:
              (A) NAME/KEY: Peptide
              (B) LOCATION: 5..19
              (D) OTHER INFORMATION: /label= peptide
                    /note= "peptide hp-28 in table 2"

(ix) FEATURE:
              (A) NAME/KEY: Peptide
              (B) LOCATION: 10..24
              (D) OTHER INFORMATION: /label= peptide
                    /note= "peptide hp-29 in table 2"

(x) PUBLICATION INFORMATION:
              (H) DOCUMENT NUMBER: US 5,030,449
              (I) FILING DATE: 21-JUL-1988
              (J) PUBLICATION DATE: 09-JUL-1991
              (K) RELEVANT RESIDUES IN SEQ ID NO:3: FROM 1 TO 20

(x) PUBLICATION INFORMATION:
              (H) DOCUMENT NUMBER: US 07/148,692
              (I) FILING DATE: 26-JAN-1988
              (K) RELEVANT RESIDUES IN SEQ ID NO:3: FROM 1 TO 20

(xi) SEQUENCE DESCRIPTION: SEQ ID NO:3:

Lys Gln Ile Ile Asn Met Trp Gln Glu Val Gly Lys Ala Met Tyr Ala
 1               5                  10                  15

Pro Pro Ile Ser Gly Gln Ile Arg
                 20

(2) INFORMATION FOR SEQ ID NO:4:

(i) SEQUENCE CHARACTERISTICS:
              (A) LENGTH: 24 amino acids
              (B) TYPE: amino acid
              (D) TOPOLOGY: linear (ii) MOLECULE TYPE: peptide (v) FRAGMENT TYPE: internal (vi) ORIGINAL SOURCE:
              (A) ORGANISM: HIV-1

(ix) FEATURE:
              (A) NAME/KEY: Peptide
              (B) LOCATION: 1..24
              (D) OTHER INFORMATION: /label= peptide
                    /note= "synthetic peptide fragment of HIV-1 gp160"

(ix) FEATURE:
              (A) NAME/KEY: Peptide
              (B) LOCATION: 1..15
              (D) OTHER INFORMATION: /label= peptide
                    /note= "peptide hp-30 in table 2"

(ix) FEATURE:
              (A) NAME/KEY: Peptide
              (B) LOCATION: 10..24
              (D) OTHER INFORMATION: /label= peptide
                    /note= "peptide hp-33 in table 2"

(x) PUBLICATION INFORMATION:
              (H) DOCUMENT NUMBER: US 5,030,449
              (I) FILING DATE: 21-JUL-1988
              (J) PUBLICATION DATE: 09-JUL-1991
              (K) RELEVANT RESIDUES IN SEQ ID NO:4: FROM 1 TO 20

(x) PUBLICATION INFORMATION:
              (H) DOCUMENT NUMBER: US 07/148,692
              (I) FILING DATE: 26-JAN-1988
              (K) RELEVANT RESIDUES IN SEQ ID NO:4: FROM 1 TO 20
```

(xi) SEQUENCE DESCRIPTION: SEQ ID NO:4:

Arg Asp Asn Trp Arg Ser Glu Leu Tyr Lys Tyr Lys Val Val Lys Ile
1               5                   10                  15
Glu Pro Leu Gly Val Ala Pro Thr
            20

(2) INFORMATION FOR SEQ ID NO:5:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: HIV-1

(ix) FEATURE:
        (A) NAME/KEY: Peptide
        (B) LOCATION: 1..34
        (D) OTHER INFORMATION: /label= peptide
            /note= "synthetic peptide fragment of HIV-1 gp160"

(ix) FEATURE:
        (A) NAME/KEY: Peptide
        (B) LOCATION: 1..15
        (D) OTHER INFORMATION: /label= peptide
            /note= "peptide hp-47 in table 2"

(ix) FEATURE:
        (A) NAME/KEY: Peptide
        (B) LOCATION: 15..29
        (D) OTHER INFORMATION: /label= peptide
            /note= "peptide hp-50 in table 2"

(ix) FEATURE:
        (A) NAME/KEY: Peptide
        (B) LOCATION: 20..34
        (D) OTHER INFORMATION: /label= peptide
            /note= "peptide hp-51 in table 2"

(x) PUBLICATION INFORMATION:
        (H) DOCUMENT NUMBER: US 5,030,449
        (I) FILING DATE: 21-JUL-1988
        (J) PUBLICATION DATE: 09-JUL-1991
        (K) RELEVANT RESIDUES IN SEQ ID NO:5: FROM 1 TO 20

(x) PUBLICATION INFORMATION:
        (H) DOCUMENT NUMBER: US 07/148,692
        (I) FILING DATE: 26-JAN-1988
        (K) RELEVANT RESIDUES IN SEQ ID NO:5: FROM 1 TO 20

(xi) SEQUENCE DESCRIPTION: SEQ ID NO:5:

Arg Ile Val Glu Leu Leu Gly Arg Arg Gly Trp Glu Ala Leu Lys Tyr
1               5                   10                  15
Trp Trp Asn Leu Leu Gln Tyr Trp Ser Gln Glu Leu Lys Asn Ser Ala
            20                  25                  30
Val Ser (2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (v) FRAGMENT TYPE: internal (vi) ORIGINAL SOURCE:
             (A) ORGANISM: HIV-1

(ix) FEATURE:
             (A) NAME/KEY: Peptide
             (B) LOCATION: 1..33
             (D) OTHER INFORMATION: /label= peptide
                 /note= "synthetic peptide fragment of HIV-1 gp160"

(ix) FEATURE:
             (A) NAME/KEY: Peptide
             (B) LOCATION: 1..15
             (D) OTHER INFORMATION: /label= peptide
                 /note= "peptide hp-52 in table 2"

(ix) FEATURE:
             (A) NAME/KEY: Peptide
             (B) LOCATION: 7..21
             (D) OTHER INFORMATION: /label= peptide
                 /note= "peptide hp-53 in table 2"

(ix) FEATURE:
             (A) NAME/KEY: Peptide
             (B) LOCATION: 9..23
             (D) OTHER INFORMATION: /label= peptide
                 /note= "peptide hp-54 in table 2"

(ix) FEATURE:
             (A) NAME/KEY: Peptide
             (B) LOCATION: 14..28
             (D) OTHER INFORMATION: /label= peptide
                 /note= "peptide hp-55 in table 2"

(ix) FEATURE:
             (A) NAME/KEY: Peptide
             (B) LOCATION: 19..33
             (D) OTHER INFORMATION: /label= peptide
                 /note= "peptide hp-56 in table 2"

(x) PUBLICATION INFORMATION:
             (H) DOCUMENT NUMBER: US 5,030,449
             (I) FILING DATE: 21-JUL-1988
             (J) PUBLICATION DATE: 09-JUL-1991
             (K) RELEVANT RESIDUES IN SEQ ID NO:6: FROM 1 TO 20

(x) PUBLICATION INFORMATION:
             (H) DOCUMENT NUMBER: US 07/148,692
             (I) FILING DATE: 26-JAN-1988
             (K) RELEVANT RESIDUES IN SEQ ID NO:6: FROM 1 TO 20

(xi) SEQUENCE DESCRIPTION: SEQ ID NO:6:

Ala Val Ala Glu Gly Thr Asp Arg Val Ile Glu Val Val Gln Gly Ala
1               5                   10                  15

Tyr Arg Ala Ile Arg His Ile Pro Arg Arg Ile Arg Gln Gly Leu Glu
            20                  25                  30

Arg

289658.B11

What is claimed is:

1. A construct comprising a first and second peptide, wherein the first peptide is a multideterminant cluster peptide of an HIV envelope protein, said peptide comprising an amino acid sequence selected from the group consisting of SEQ ID NO1, SEQ ID NO:2, SEQ ID NO:4, SEQ ID NO:5, and SEQ ID NO:6, wherein the second peptide contains a T- or a B- cell epitope; and wherein said first peptide is coupled to said second peptide by chemical coupling or is co-synthesized with said second peptide.

2. The construct of claim 1, wherein said first peptide is 20 to 34 amino acids in length.

3. A multideterminant cluster peptide of an HIV envelope protein, said peptide comprising an amino acid sequence selected from the group consisting of SEQ ID NO:2, SEQ ID NO:4, SEQ ID NO:5, and SEQ ID NO:6.

4. The peptide of claim 3, wherein said peptide consists of the amino acid sequence of SEQ ID NO:4.

5. The peptide of claim 3, wherein said peptide consists of the amino acid sequence of SEQ ID NO: 6.

6. The peptide of claim 3, wherein said peptide consists of the amino acid sequence of SEQ ID NO:2.

7. The peptide of claim 3, wherein said peptide consists of the amino acid sequence of SEQ ID NO:5.

8. The peptide of claim 3, wherein said peptide is 20–34 amino acids in length.

9. A construct comprising a first peptide which comprises an amino acid sequence selected from the group consisting of SEQ ID NO: 1, SEQ ID NO: 2, SEQ ID NO: 3, SEQ ID NO: 4, SEQ ID NO: 5, and SEQ ID NO: 6 chemically coupled to or co-synthesized with a second peptide comprising a T-cell or B-cell epitope.

10. A construct comprising a first and second peptide,
wherein the first peptide is a multideterminant cluster peptide of an HIV envelope protein consisting of the amino acid sequence of SEQ ID NO:3, wherein the second peptide contains a T- or a B- cell epitope; and wherein said first peptide is coupled to said second peptide by chemical coupling or is co-synthesized with said second peptide.

11. A multideterminant cluster-peptide, of an HIV envelope protein, said peptide consisting of the amino acid sequence of SEQ ID NO:3.

12. A multideterminant cluster peptide of an HIV envelope protein, said peptide consisting of the amino acid sequence of SEQ ID NO: 1.

* * * * *